United States Patent
Wang et al.

(10) Patent No.: US 10,299,729 B2
(45) Date of Patent: May 28, 2019

(54) HEART RATE DETECTION WITH MULTI-USE CAPACITIVE TOUCH SENSORS

(71) Applicant: Google Inc., Mountain View, CA (US)

(72) Inventors: Jingtao Wang, Pittsburgh, PA (US); Shumin Zhai, Los Altos, CA (US)

(73) Assignee: Google LLC, Mountain View, CA (US)

(*) Notice: Subject to any disclaimer, the term of this patent is extended or adjusted under 35 U.S.C. 154(b) by 70 days.

(21) Appl. No.: 14/921,134

(22) Filed: Oct. 23, 2015

(65) Prior Publication Data
US 2017/0112445 A1    Apr. 27, 2017

(51) Int. Cl.
| | | |
|---|---|---|
| G06F 3/041 | (2006.01) | |
| A61B 5/02 | (2006.01) | |
| A61B 5/0402 | (2006.01) | |
| G06F 7/04 | (2006.01) | |
| A61B 5/00 | (2006.01) | |
| G06F 3/0488 | (2013.01) | |

(Continued)

(52) U.S. Cl.
CPC .......... *A61B 5/6898* (2013.01); *A61B 5/0245* (2013.01); *A61B 5/02438* (2013.01); *A61B 5/486* (2013.01); *A61B 5/725* (2013.01); *A61B 5/7257* (2013.01); *A61B 5/7278* (2013.01); *A61B 5/7445* (2013.01); *A61B 5/7475* (2013.01); *G06F 3/0416* (2013.01); *G06F 3/0488* (2013.01); *A61B 2562/0214* (2013.01); *G06F 3/044* (2013.01)

(58) Field of Classification Search
CPC .. A61B 5/02438; A61B 5/0245; A61B 5/0404
USPC ........................................................ 600/509
See application file for complete search history.

(56) References Cited

U.S. PATENT DOCUMENTS

| | | | |
|---|---|---|---|
| 2010/0113950 A1 | 5/2010 | Lin et al. | |
| 2014/0121982 A1* | 5/2014 | Rauhala | A61B 5/6898 702/19 |
| 2014/0362013 A1 | 12/2014 | Nikoozadeh et al. | |

FOREIGN PATENT DOCUMENTS

EP    2656783 A1    10/2013

OTHER PUBLICATIONS

Peng, Jen-Yu and Lu, Michael S.-C., A Flexible Capacitive Tactile Sensor Array With CMOS Readout Circuits for Pulse Diagnosis, IEEE Sensors Journal, Feb. 2015, pp. 1170-1177, vol. 15, No. 2, IEEE Service Center, New York, NY, US.

(Continued)

*Primary Examiner* — Jon Eric C Morales
(74) *Attorney, Agent, or Firm* — Colby Nipper

(57) ABSTRACT

This document describes heart rate detection with multi-use capacitive touch sensors. Fluctuations in capacitance are detected (802) using capacitive touch sensors. These capacitive touch sensors are also used to detect touch inputs to control operations of a computing device. When contact of a person's hand with the computing device is detected, the capacitive touch sensors produce raw capacitance data that indicates detected capacitance fluctuations. The raw capacitance data is extracted (902) from the capacitive touch sensors using a modified device driver that bypasses default driver configurations that ignore fluctuations in capacitance due to heartbeats. Times during which the person's hand contacts the computing device and locations of the contact are determined (804) from the raw capacitance data indicative of the fluctuations. The extracted raw capacitance data is then processed to determine the person's heart rate (806, 808).

20 Claims, 9 Drawing Sheets

(51) Int. Cl.
*A61B 5/0245* (2006.01)
*A61B 5/024* (2006.01)
*G06F 3/044* (2006.01)

(56) References Cited

OTHER PUBLICATIONS

PCT/US2016/058049 International Search Report and Written Opinion dated Feb. 7, 2017.
"Foreign Office Action", European Application No. 16791737.6, dated May 30, 2018, 3 pages.
"International Preliminary Report on Patentability", PCT Application No. PCT/US2016/058049, dated Apr. 24, 2018, 9 pages.

\* cited by examiner

HEART RATE DETECTION WITH MULTI-USE CAPACITIVE TOUCH SENSORS

BACKGROUND

Heart rate is the speed of the heartbeat measured by a number of poundings per unit of time—typically beats-per-minute ("BPM"). In healthcare, fitness training, and stress management as well as in emerging emotion-aware and affect-aware user interfaces, heart rate is a useful physiological signal. Conventional techniques for monitoring heart rate typically use dedicated sensors, such as electrocardiogram ("ECG") sensors and blood oxygen sensors (e.g., oximeters), embedded in specialized devices having form factors such as wristbands, watches, and chest bands. Such conventional deployments, however, are rife with inconveniences to users. Associated with these conventional techniques, for example, are costs of the devices, discomfort from wearing them, or effort required to employ them. As a result of these inconveniences, heart rates simply are not monitored, analyzed, or used in the normal course of most people's lives.

SUMMARY

This document describes heart rate detection with multi-use capacitive touch sensors. Detection of a heart rate with multi-use capacitive touch sensors involves detecting fluctuations in capacitance that arise in a person's hand due to heartbeats using capacitive touch sensors that are also used to detect touch inputs to control operations of a computing device, e.g., taps on a display component to type messages via a displayed keyboard. These capacitive touch sensors produce raw capacitance data that is indicative of contact made by a person's hand (e.g., one or more fingers) with the computing device, including the fluctuations in capacitance due to the person's heartbeats. A heart rate detection manager determines times during which the person's hand contacts the computing device and locations on the computing device at which the contact is made. To do so, the heart rate manager analyzes the capacitance fluctuations and the times of those fluctuations as indicated by the raw capacitance data to determine which fluctuations correspond to contact made by the person's hand as opposed to noise, such as fluctuations in capacitance caused by an alternating current ("AC") charger, liquid crystal display ("LCD"), environmental electromagnetic interference, or other artifacts.

To extract the raw data from the capacitive touch sensors, a modified device driver bypasses default configurations in touchscreen firmware and device drivers that cause fluctuations in capacitance below a certain amplitude to be ignored. Accordingly, the extracted raw capacitance data indicates the fluctuations in capacitance due to heartbeats, noise caused by an AC charger, LCD, environmental electromagnetic interference, or other artifacts. After the raw capacitance data is extracted from the capacitive touch sensors, the heart rate detection manager processes the raw capacitance data to determine the person's heart rate. In so doing, the heart rate detection manager isolates heartbeat waveforms from interferences in the extracted capacitance data. It then analyzes the heartbeat waveforms to determine the person's heart rate. A benefit of these techniques is that they enable a person's heart rate to be determined, and thus monitored, in the normal course of interacting with a capacitive touchscreen. By way of example, these techniques determine heart rates while people interact with their mobile phones, e.g., texting, playing games, browsing through social media, and so on. As such, these techniques enable heart rates to be monitored, analyzed, and used regularly—not just when a specialized device, the primary purpose of which is to monitor a person's heart rate, is deployed.

This summary introduces simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for heart rate detection with multi-use capacitive touch sensors are described with reference to the following drawings. Throughout the drawings the same numbers are used to reference like features and components.

DETAILED DESCRIPTION

Overview

Figure 1:
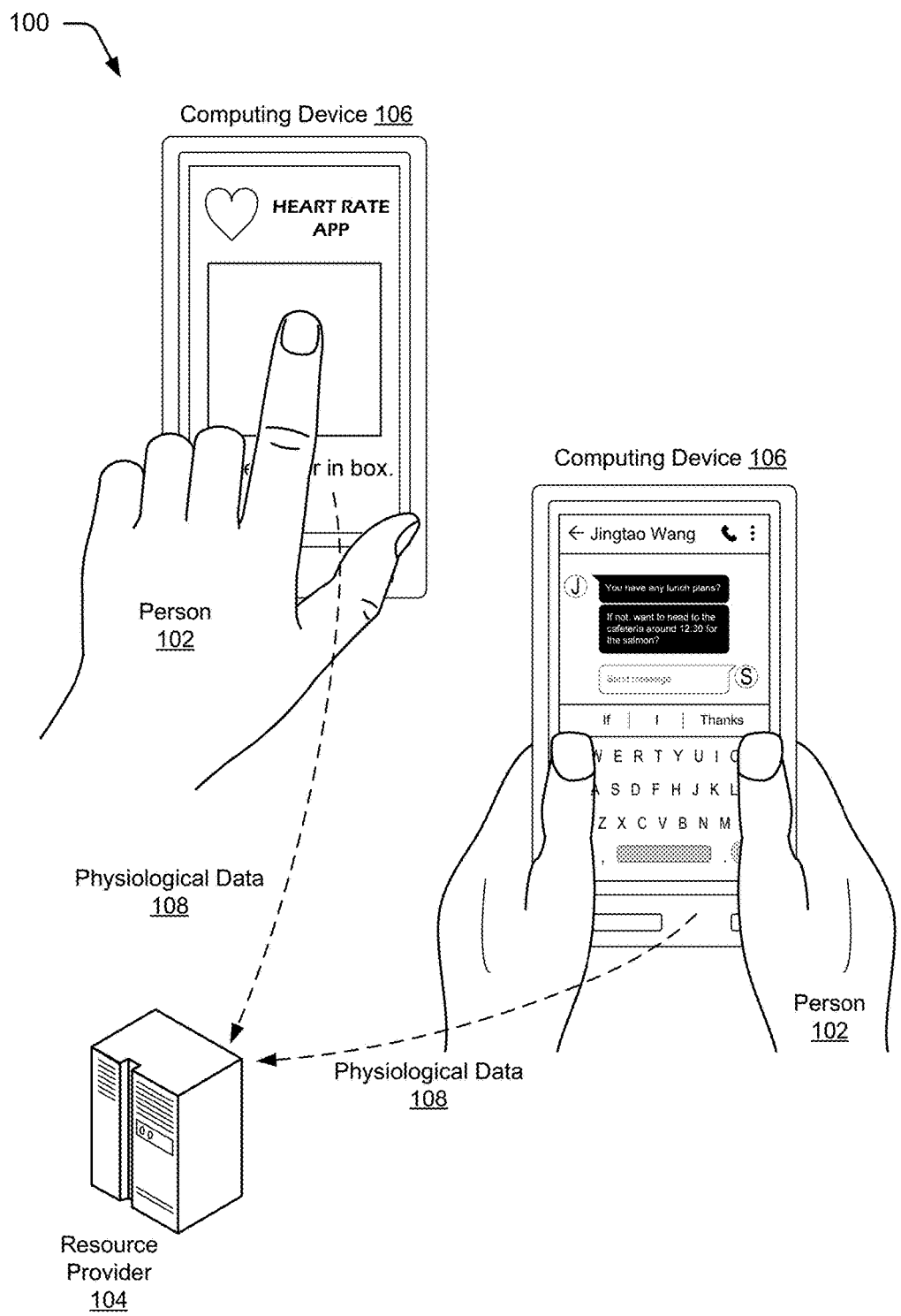
FIG. 1 illustrates an example environment in which the techniques can be implemented.

This document describes techniques using, and devices enabling, heart rate detection with multi-use capacitive touch sensors. These techniques and devices, determine a person's heart rate without deploying specialized devices for the purpose of determining heart rate. Instead, the techniques described herein determine heart rates through interactions people have with devices equipped with capacitive touch sensors in the normal course of their everyday lives. Through wide application of these techniques, peoples' heart rates can be determined regularly, resulting in improved healthcare, personal well-being, emotion-aware interfaces, and so on.

By way of example, a person can interact with a mobile phone via touch input to utilize its functionality, such as functionality to send and receive messages (e.g., text messages, emails, instant messages, and so on), play games, browse web pages on the Internet, browse social networks, hold the device when display functionality of a presence-sensitive display component is in a power saving mode (e.g., locked, sleeping, hibernating, off, etc.), and so on. When a person's hand makes contact with the mobile phone during such interactions, capacitive touch sensors of the mobile phone can detect fluctuations in capacitance that result from the contact. Responsive to detection of these fluctuations, the capacitive touch sensors produce raw capacitance data that is indicative of them—the raw capacitance data indicates locations on the mobile phone where the fluctuations in capacitance occurred and their times.

When implementing functionality controlled by the touch inputs, conventionally configured device touch sensor firmware and drivers extract data from capacitive touch sensors that is filtered to ignore what is considered noise—including the capacitance fluctuations that result from a person's heartbeat, an AC charger, an LCD, another nearby electronic device such as a fluorescent light bulb, environmental electromagnetic interference, or other artifacts. To this extent, the capacitance data provided to applications to implement mobile phone functionality indicate just the location and the contact region size of touch inputs received. It does not indicate "noise" such as capacitance fluctuations due to a person's heartbeat which, unlike touch inputs, are not used to control functionality of the mobile phone. In contrast to conventional techniques, the techniques herein employ a modified device driver to extract the raw capacitance data from the capacitive touch sensors, which indicates the fluctuations in capacitance of a person's hand that are due to the person's heartbeat. This information is then processed to isolate heartbeat waveforms, which can be analyzed to determine a person's heart rate.

Thus, with no user effort beyond performing everyday interactions with a mobile phone, a person's heart rate can be determined, analyzed and used in a variety of different ways. When performed on a repeated basis and over a period of time (e.g., daily for a week, weeks, or months), for example, this act can be used to assess a person's stress level. Consider a situation where, over the course of a month, using heart rates determined with data extracted from the multi-use capacitive touch sensors, a device indicates a person's stress level is reduced on days when the person also goes to the gym. With this positive feedback, this person may continue their exercise routine, thereby likely reducing stress levels and leading to improved overall health.

This is but one simple example of ways in which heart rate detection with multi-use capacitive touch sensors can be performed and utilized; other examples and details are provided below. This document now turns to an example environment, after which this document describes example devices and methods for implementing heart rate detection with multi-use capacitive touch sensors and an example computing system.

Example Environment

FIG. 1 illustrates an example environment 100 in which heart rate detection with multi-use capacitive touch sensors can be employed. Environment 100 illustrates hands of a person 102 that is the subject of the heart rate detection, as well as a resource provider 104 that, in some cases, receives information about the person 102's heart rate to provide them with heart rate based services. This example employs computing device 106 that is capable of detecting heart rate with multi-use capacitive touch sensors. In the particular example of FIG. 1, the computing device 106 is configured as a smartphone, however, other configurations are contemplated. Later figures illustrate other configurations of the computing device 106 for detecting heart rate with multi-use capacitive touch sensors.

Physiological data 108 is communicable from the computing device 106 to other entities, such as the resource provider 104, other computing devices remote from the computing device (not shown), and so on. The physiological data 108 includes data indicative of the person 102's heart rate at different times, heartbeat waveform data that can be generated from raw capacitance data extracted from capacitive touch sensors of the computing device, and so forth. Additionally or alternately, the physiological data 108 includes the raw capacitive data that is extracted from the capacitive touch sensors. This raw sensor data can be communicated to the resource provider 104 to isolate the heartbeat waveforms and determine the heart rate of the person 102. By doing so, the computing burden of determining heart rate from the raw sensor data can be offloaded from the computing device 106.

As shown with this example environment 100, the person 102 can interact with the computing device 106 in different ways yet still have heart rate determined. In one of the two examples illustrated in FIG. 1, the person 102's heart rate is determined "explicitly". As used herein, an "explicit" determination of the person 102's heart rate involves display of a user interface that prompts the person 102 to place a portion of his or her hand (e.g., a finger) on the computing device 106 for the expressed purpose of determining heart rate. This explicit determination may be made, for example, when the person 102 accesses a heart rate monitoring application as illustrated. Such an application may be launched automatically at a pre-determined time or times each day to determine the person 102's heart rate. In addition to determining heart rate "explicitly," an "implicit" determination of the person 102's heart rate can also be made. The other of the two examples in FIG. 1 illustrates an implicit determination of the person 102's heart rate. Broadly speaking, an implicit determination of the person 102's heart rate involves making the determination in the background of another interaction with the computing device 106. In other words, the person 102's heart rate is determined while he or she interacts with the computing device 106 in ways other than for the specific purpose of determining heart rate, such as while interacting with the computing device 106 to send and receive messages, as illustrated.

Figure 2:
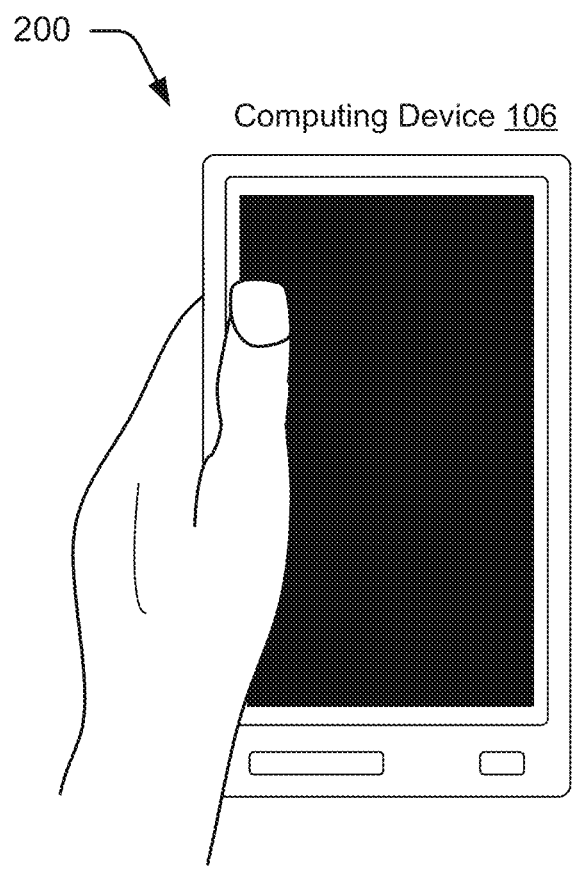
FIG. 2 illustrates another example of the computing device of FIG. 1 configured to determine a person's heart rate using multi-use capacitive touch sensors while display functionality of a screen of the computing device is in a power saving mode.

FIG. 2 illustrates another example 200 of the computing device of FIG. 1 that is configured to determine a person's heart rate using multi-use capacitive touch sensors, but while display functionality of a screen of the computing device is in a power saving mode. The example 200 depicts the computing device 106 with a blank screen. The blank screen of the computing device 106 in the example 200 represents another manner of implicitly determining the person 102's heart rate. In particular, the example 200 represents a scenario in which the computing device 106 determines the person 102's heart rate while display functionality of the screen is in a power saving mode, e.g., while the person 102 merely holds the computing device 106 and touches a finger to the screen. As used herein, the phrase "in a power saving mode" refers to scenarios in which the screen of the computing device 106 is in a hibernation mode, a locked mode, is not illuminated, is simply off, and the like.

In other words, the example 200 represents scenarios in which the screen of the computing device 106 displays a minimal amount of content (e.g., graphical elements for unlocking the computing device 106, a time, battery life, and so forth), if any, for user interaction. Despite the screen being in a power saving mode, the techniques described herein still use the capacitive touch sensors to determine the person 102's heart rate.

Conventionally-configured devices measure heart rate using a variety of specialized sensors or detection technologies, such as electrocardiogram (ECG) sensors, photoplethysmography (PPG) sensors, commodity camera based heart rate sensing, heart rate sensing via radar signals, and so on. Generally, ECG-configured devices use multiple electrodes in direct contact with a user's skin to detect weak electric signals generated by heartbeats. To detect high-quality ECG signals, an ECG-configured device must usually be placed tightly against specific regions of a user, such as against a user's chest or both arms, which can lead to inconveniences or discomfort during extended use. PPG sensors, such as blood oxygen sensors, oximeters, or optical heart rate sensors, use light emitters and optical sensors to capture changes to skin tissue transparency during cardiac cycles. Drawbacks of using PPG sensor-configured devices include, their cost, the requirement of tight contact with skin, and battery consumption of the PPG sensors. Commodity camera based heart rate sensing uses cameras, such as front and back cameras of phones, to measure heart rate. In particular, commodity camera based heart rate sensing extracts heart rates from skin color change signals and involuntary motion generated by heartbeats. To extract heart rates, however, a region of interest such as fingertips or faces must stay in a viewport of the camera without major motion during the measurement. Conventional techniques that sense heart rates using radar signals monitor wireless interference caused by heartbeats. Such interference can be detected by sending, receiving, and analyzing modulated radio signals from dedicated wireless transmitters. Such an approach employs large and costly customized wireless transmitters and its application requires a user to sit still and to be at least a minimum distance away from other vital objects.

In contrast, the computing device 106 is capable of detecting fluctuations in capacitance due to heartbeats of the person 102 without employing such specialized sensors or detection technologies. Instead, the computing device 106 simply uses capacitive touch sensors to detect fluctuations in capacitance due to the person 102's heartbeat, e.g., fluctuations in capacitance from a portion of the person 102's hand. Capacitive touch sensors often have a sampling rate of 30-100 Hz. This sample rate is higher than sample rates of camera based heart rate detection techniques, and higher sampling rates typically lead to better signal recovery and higher Signal-to-Noise Ratio (SNR) than lower ones. Capacitive touch sensors are thus more suitable for determining heart rates than those employed for the camera based heart rate detection techniques. Accordingly, the computing device 106 employs the capacitive touch sensors to detect the fluctuations in capacitance due to the person 102's heartbeat in either an explicit or implicit manner as described herein. Responsive to detection of these fluctuations, the capacitive touch sensors of the computing device 106 produce raw capacitance data indicative of the detected fluctuations. The computing device 106 is capable of extracting the raw capacitance data from the capacitive touch sensors and processing the extracted data to determine the person 102's heart rate, as described herein below.

Figure 3:
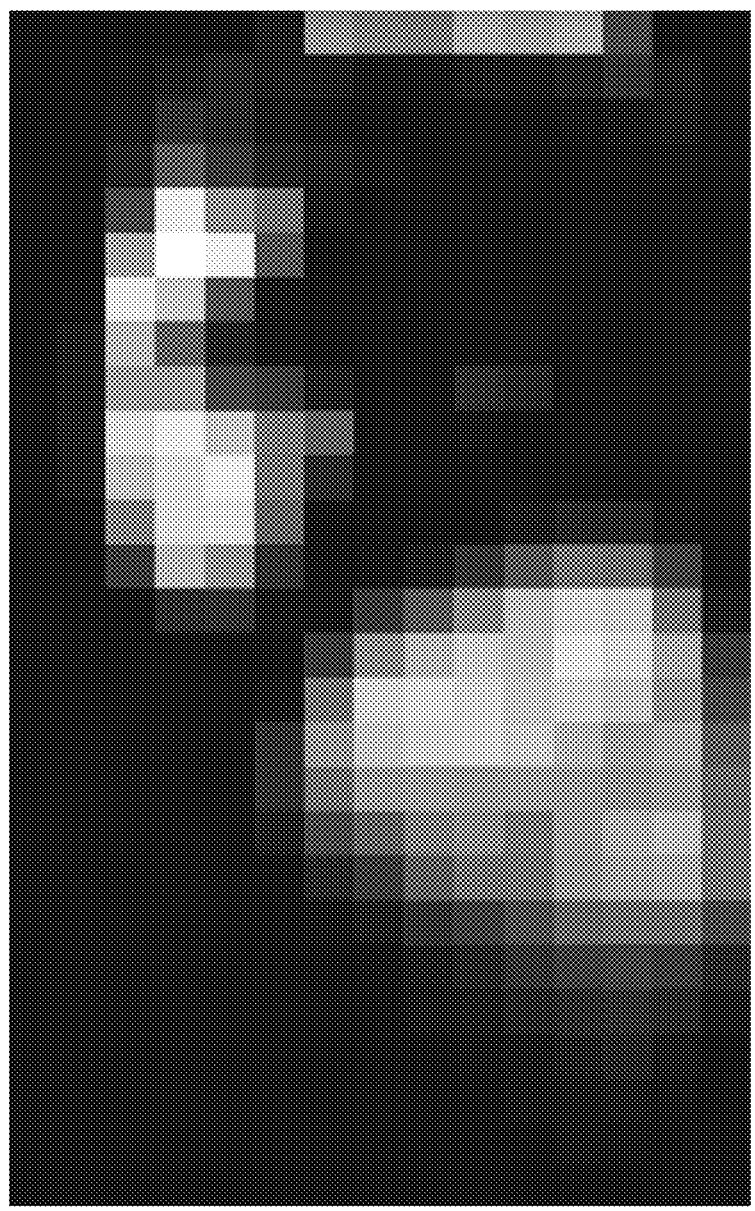
FIG. 3 illustrates an example of raw two-dimensional capacitance readings produced by multi-use capacitive touch sensors for the screen of the computing device.

FIG. 3 depicts raw two-dimensional (2D) capacitance readings 300 produced by capacitive touch sensors. For example, capacitive touch sensors of the computing device 106 can produce the raw 2D capacitance readings 300 for a presence-sensitive display component of the computing device 106. In one or more implementations, the capacitive touch sensors save the raw 2D capacitance readings 300 in 15 by 27 by 16 bit 2D arrays. Regardless of how the raw 2D capacitance readings are saved, the computing device 106 is capable of extracting these readings from the capacitive touch sensors to determine the person 102's heart rate.

The determined heart rate can then be used for a variety of purposes, such as to display the heart rate to the person 102, communicate content to the person 102 (e.g., send the person 102 advertising content for vacations when the determined heart rate indicates a high level of stress, send the person 102 images of cute napping puppies wearing hats, and so forth), increase an amount of error-correction performed (e.g., when the determined heart rate indicates a high level of stress and thus also a greater likelihood that the person 102 will make errors during interactions with the computing device 106, such as typographical errors), and so on.

Figure 4:
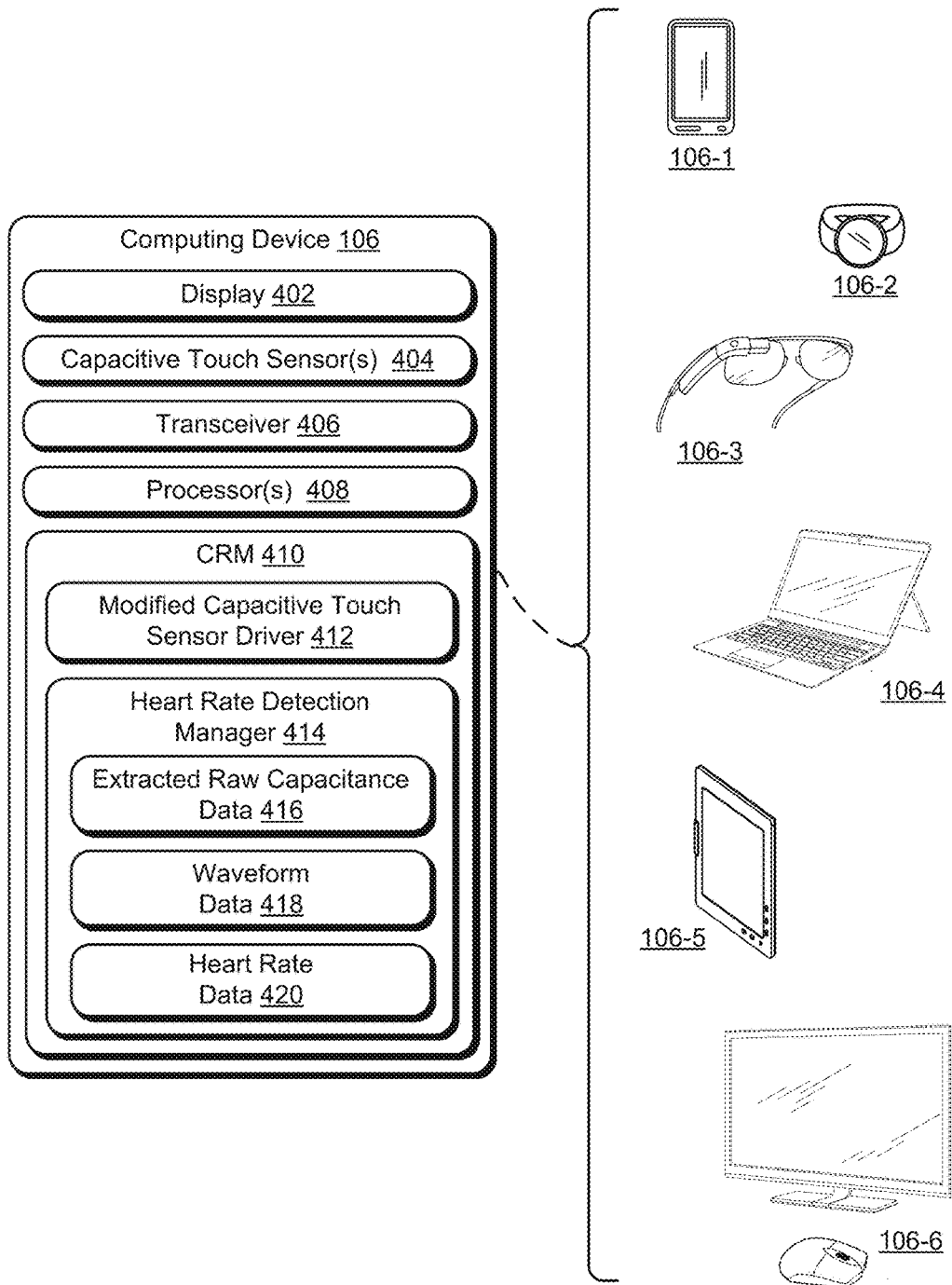
FIG. 4 illustrates an example computing device of FIG. 1 that is configured to determine a person's heart rate using multi-use capacitive touch sensors and in further detail.

With regard to the example computing device 106 of FIG. 1, consider a detailed illustration in FIG. 4. The computing device 106 can also be implemented as one or a combination of various devices, here illustrated with six examples: a smartphone 106-1, a computing watch 106-2, computing spectacles 106-3, a laptop 106-4, a tablet computer 106-5, and a desktop with a mouse 106-6, though other computing devices and systems, such as a netbook, remote controller, e-book, or a set-top box may also be used. As noted above, in some embodiments the techniques operate, in whole or in part, through a remote device. The remote computing device can be configured as a server, for example. In such cases, some computing can be forgone locally, e.g., through a communication device having limited computing operations or even directly from devices 106 to the server.

The computing device 106 includes or is able to communicate with a display 402 (six are shown in FIG. 4), one or more capacitive touch sensors 404, a transceiver 406, one or more processors 408, and computer-readable storage media 410 (CRM 410). The transceiver 406 is capable of sending and receiving data, such as the physiological data 108 from the devices 106, directly or through a communication network such as a local area network, wide area network, or personal area network using any of a variety of wired or wireless communications protocols such as Ethernet, cellular, WiFi, NFC, infrared, and others.

The capacitive touch sensors 404 represent functionality of the computing device 106 to detect fluctuations in capacitance and produce raw capacitance data indicative of the detected capacitance fluctuations. By way of example, the display 402 of the computing device 106 can be configured with the capacitive touch sensors 404 to create a presence-sensitive display component (e.g., a touchscreen) so that contact made by the person 102's hand on top of the display 402 is detected. Such functionality can be utilized to receive touch input via the display 402 configured as the presence-sensitive display component to control operations of the computing device 106, such as tapping inputs to select letters on a displayed keyboard for writing messages, swiping gestures to move displayed portions of a user interface over or off the display, multi-finger inputs to perform zooming or rotating of a displayed object, and so on. Not only are the capacitive touch sensors 404 capable of detecting fluctuations in capacitance due to such touch inputs, but they are also capable of detecting subtler fluctuations in capacitance, such as involuntary fluctuations that occur in fingers of the person 102 as a result of the person 102's heartbeat.

Regarding capacitance fluctuations due to a heartbeat, a person's heart pumps fresh blood to blood vessels throughout his or her body in every cardiac cycle. This includes pumping blood to the person's fingertips in every cycle. The arrival of blood to a fingertip causes a change in dielectric constant of the fingertip. Such a change, although subtle, is detectable by the capacitive touch sensors 404 of the computing device 106 as a fluctuation in capacitance.

As a result of detecting capacitance fluctuations, both those that occur due to intentionally made touch inputs to control operations of the computing device 106 and those that occur due to other events, such as the person 102's beating heart, an AC charger, an LCD, another nearby electronic device such as a fluorescent light bulb, environmental electromagnetic interference, or other artifacts, the capacitive touch sensors 404 produce raw capacitance data indicative of the fluctuations detected. The raw capacitance data produced can describe location information of the capacitive fluctuations, e.g., where the computing device 106 was contacted by the person 102's hand. The raw capacitance data can also describe timing of the capacitive fluctuations, e.g., timestamps can be associated with times when the person 102's hand makes contact with the computing device 106 and when the contact is terminated.

Although the examples described herein primarily involve configurations of the computing device 106 in which the capacitive touch sensors 404 detect contacts made relative the display 402 (e.g., for the presence-sensitive display component), the computing device 106 may alternatively or in addition be configured with capacitive touch sensors to detect contact made by the person 102 elsewhere. For example, the computing device 106 may include one or more of the capacitive touch sensors 404 along a back or side housing of the computing device 106. By configuring the computing device 106 in this way, the capacitive touch sensors 404 can detect fluctuations in capacitance while the computing device 106 is simply held in the person 102's hand, such as fluctuations in capacitance that occur in the person 102's palm. In addition to detecting capacitance fluctuations for a portion of the person 102's hand, the capacitive touch sensors 404 can also be used to detect heartbeat-caused capacitance fluctuations that occur at other parts of the person 102's body. The capacitive touch sensors 404 can detect fluctuations that occur in the person 102's leg when the computing device 106 is placed in a pocket of pants worn by the person 102, for example. The capacitive touch sensors 404 are capable of detecting capacitance fluctuations due to the person 102's heartbeat from a variety of different parts of his or her body without departing from the spirit or scope of the techniques described herein.

The CRM 410 includes modified capacitive touch sensor driver 412 and heart rate detection manager 414 ("HR detection manager 414"), which includes or has access to extracted raw capacitance data 416, waveform data 418, and heart rate data 420. The extracted raw capacitance data 416 is extracted from the capacitive touch sensors 404 by the modified capacitive touch sensor driver 412. As discussed above, conventionally configured device drivers filter capacitance data that is extracted from capacitive touch sensors to ignore subtler capacitance fluctuations, such as those due to a person's heartbeat. In other words, conventionally configured device drivers for capacitive touch sensors treat capacitance fluctuations due to heartbeat as "noise". In so doing, the conventionally configured device drivers for capacitive touch sensors eliminate the capacitance fluctuations due to heartbeats in the process of converting a two-dimensional (2D) map of raw capacitance indications to (x, y) locations of fingers.

Unlike conventionally configured device drivers, the modified capacitive touch sensor driver 412 extracts the raw capacitance data, produced by the capacitive touch sensors 404, for processing by other components of the computing device 106. To do so, the modified capacitive touch sensor driver 412 may bypass conventional configurations of firmware and device drivers that ignore fluctuations in capacitance due to heartbeats, AC charger noise, LCD noise, electromagnetic interference noise, and other artifacts. In this way, the extracted raw capacitance data 416 that is indicative of the person 102's heartbeat can be made available to the HR detection manager 414. Not only does the HR detection manger 414 represent functionality to process the extracted raw capacitance data 416 to determine the person 102's heart rate, but it also represents functionality to employ the modified capacitive touch sensor driver 412 to extract the raw capacitance data 416. Said another way, the HR detection manager 414 can control which portions of the raw capacitance data the modified capacitive touch sensor driver 412 extracts from the capacitive touch sensors 404.

For example, the HR detection manager 414 can instruct the modified capacitive touch sensor driver 412 to extract the raw capacitance data, configured as two-dimensional (2D) capacitance readings, for a fixed-size region around the locations at which the person 102's hand (such as one or more fingers) is determined to contact the computing device 106. In one or more embodiments, the fixed-size region is a one inch by one inch region around the determined contact locations. The raw capacitance data extracted from the capacitive touch sensors 404 can then be saved as the extracted raw capacitance data 416. For each frame of the extracted raw capacitance data 416, the modified capacitive touch sensor driver 412 can cause a corresponding timestamp to be saved in association therewith.

The HR detection manager 414 also represents functionality to determine times and locations that at least a portion of the person 102's hands contact the computing device. To do so, the HR detection manager 414 analyzes the capacitance fluctuations and the times of those fluctuations as indicated by the extracted raw capacitance data 416 to determine which fluctuations correspond to contact made by the person 102's hand as opposed to noise, such as fluctuations in capacitance caused by an alternating current (AC) charger, liquid crystal display (LCD), environmental electromagnetic interference, or other artifacts. Generally, "regular" human heart rates (when resting, sedentary, walking, and up to cooling down after exercise) are within a range of 1-3 Hz (60 to 180 beats-per-minute ("BPM")). In contrast, "extreme" human heart rates can range from 0.5-4 Hz (30 to 240 BPM). With regard to determining times, for instance, the HR detection manager 414 is capable of determining landing and departure timestamps of a finger of the person 102 on the display 402 of the computing device 106, e.g., using touch events such as POINTER_DOWN and POINTER_UP. With regard to determining contact locations, the HR detection manager 414 is capable of using thresholding techniques to determine one or more points where the person 102 contacts touch-enabled interfaces of the computing device 106.

From the extracted raw capacitance data 416, the HR detection manager 414 is configured to isolate heartbeat waveforms, which can be used to generate the waveform data 418. As part of doing so, the HR detection manager 414 sums indications of the capacitance in each frame of the extracted raw capacitance data 416. The HR detection manager 414 uses the sum of indications for each frame of the extracted capacitance data 416 to generate a one-dimensional (1D) aggregated capacitance for the frame. The HR detection manager 414 then arranges the 1D aggregated capacitance generated for each of the frames against the corresponding times, e.g., according to the timestamps stored in association with the extracted raw capacitance data 416. In one or more embodiments, the HR detection manager 414 applies a band pass filter to the 1D aggregated capacitances to eliminate interference from sources other than the person 102's heartbeat, such as an AC charger, an LCD, environmental electromagnetic interference, pressure, motion, wireless interference, or other artifacts.

Figure 5:
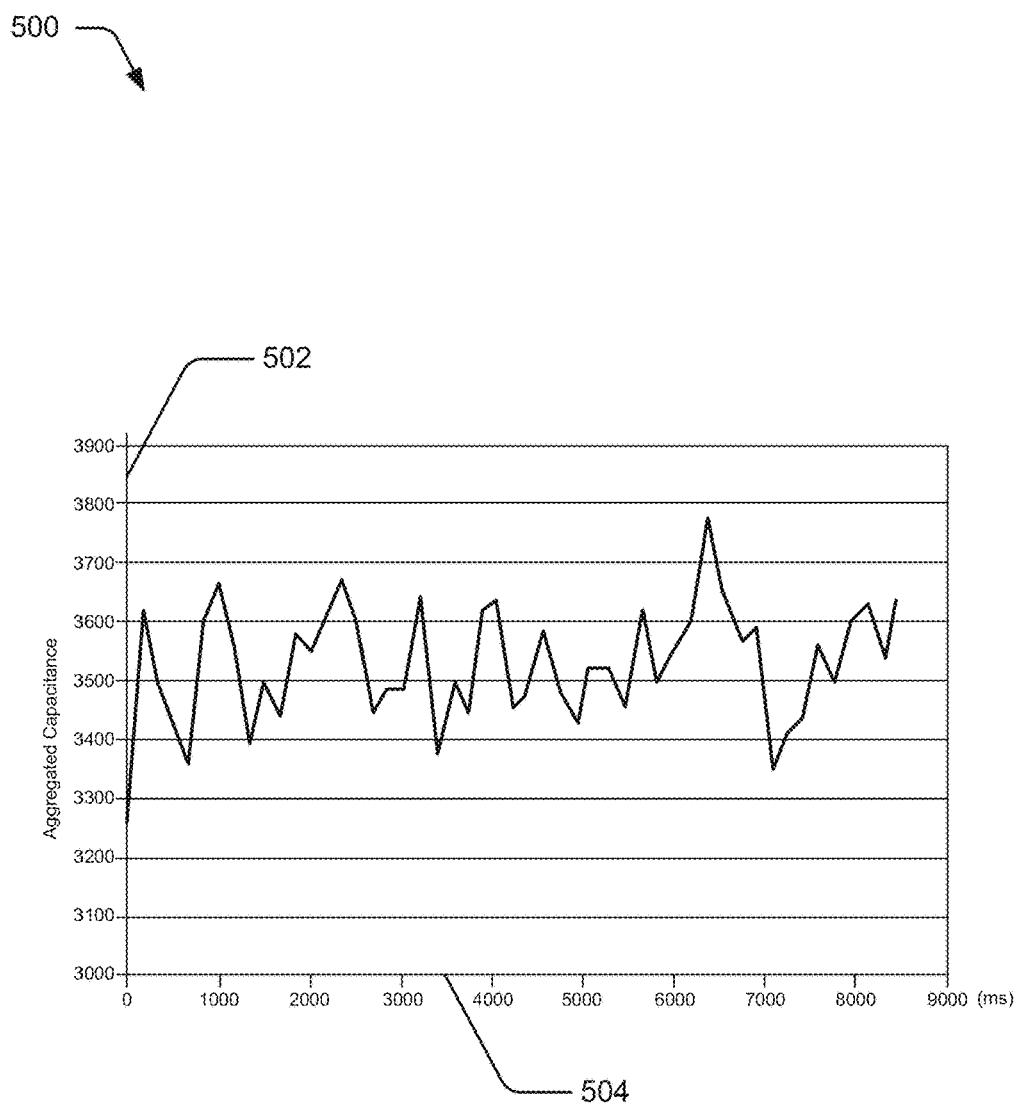
FIG. 5 illustrates an example heartbeat waveform isolated from raw capacitance data that is extracted from the capacitance sensors and from which a heart rate can be determined.

For context, consider FIG. 5, which illustrates an example of a heartbeat waveform that can be isolated from the raw capacitance data extracted from capacitive touch sensors. The example heartbeat waveform 500 indicates aggregated capacitance along a y-axis 502 and elapsed time along an x-axis 504. Data indicative of such waveforms can be maintained as the waveform data 418. Through an analysis of the example heartbeat waveform 500 (and other heartbeat waveforms maintained as part of the waveform data 418), the HR detection manager 414 can determine a heart rate of the person 102.

To determine the person 102's heart rate from the waveform data 418, the HR detection manager 414 can apply a variety of different techniques. As one example, the HR detection manager 414 determines the person 102's heart rate directly from a 1D temporal signal indicated in the waveform data 418 by ascertaining peaks and valleys of the generated heartbeat waveforms. In addition or alternately, the HR detection manager 414 makes a determination of the person 102's heart rate in the frequency domain. To do so, the HR detection manager 414 applies a Fast Fourier Transform (FFT) to the 1D aggregated capacitances. The HR detection manager 414 then thresholds a result of applying the FFT in the frequency domain to determine the person 102's heart rate.

In one or more embodiments, the HR detection manager 414 also applies post processing heuristics to ensure that the determined heart rate falls within a valid range of heart rates, e.g., 30 beats-per-minute ("BPM") to 180 BPM. This inherently removes frequencies that are commonly electronic device noise (e.g., 60 Hz and higher frequencies). In addition or alternatively, the HR detection manager 414 applies the post processing heuristics to ensure that the change between adjacent heart rate readings is small by eliminating outliers or applying a fixed-size smoothing window to the determined heart rate.

After the heart rate is determined, the HR detection manager 414 can generate data indicative of the determined heart rate and maintain that data as the heart rate data 420. The heart rate data 420 can be associated with timestamps to indicate a time at which the person 102's heart rate is determined. By way of example, a determined heart rate can be associated with a time that the raw capacitance data used to determine the heart rate was produced by the capacitive touch sensors 404. The extracted raw capacitance data 416, the waveform data 418, and the heart rate data 420 corresponding to the raw capacitance data used may also be associated with the timestamp.

Raw capacitance data that is produced at a different time, say after the above-discussed raw capacitance data is produced, can be associated with a different timestamp. Accordingly, the extracted raw capacitance data 416, the waveform data 418, and the heart rate data 420 that corresponds to or is generated from this second portion of the raw capacitance data can be associated with the different timestamp. In so doing, the heart rates determined and maintained as the heart rate data 420 can be compared over time.

In addition to determining the person 102's heart rate implicitly (in the background while the person 102 interacts with the computing device 106 for purposes other than determining heart rate), the techniques described herein can also determine the person 102's heart rate explicitly. By way of example, the computing device 106 may launch a heart rate monitoring application for the expressed purpose of determining the person 102's heart rate. The computing device 106 may do so responsive to a user selection to launch the application or automatically and without receiving a user selection to launch the application at the time of launch, e.g., the application may be launched at predetermined intervals so that a determination of the person 102's heart rate is made on a regular basis.

Figure 6:
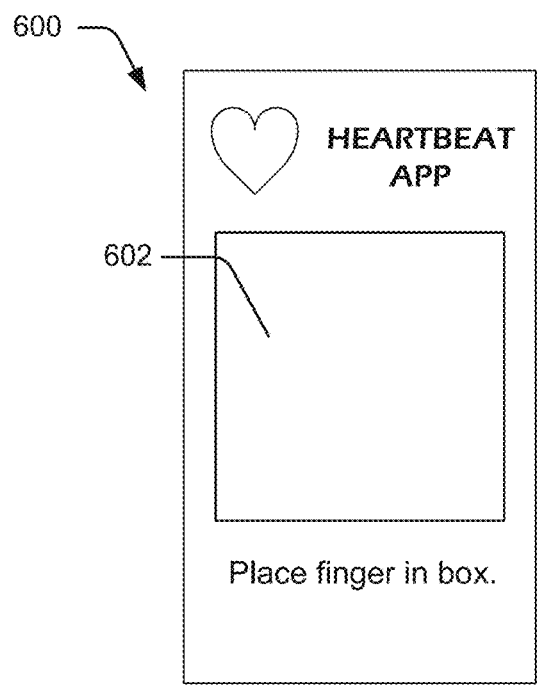
FIG. 6 illustrates an example of a user interface presented by a heart rate monitoring application to capture information for determining a person's heart rate.
Figure 7:
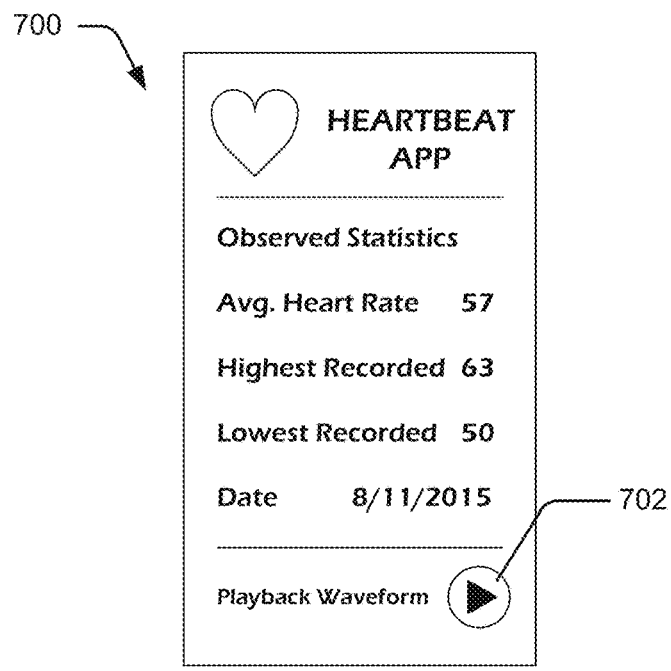
FIG. 7 illustrates an example of another user interface presented by the heart rate monitoring application that displays information about the person's determined heart rate.

With regard to application user interfaces that can be used in conjunction with determining the person 102's heart rate in an explicit manner, consider the illustrations in FIGS. 6 and 7. FIG. 6 depicts a user interface 600 that prompts the person 102 to place a portion of his or her hand (finger) on a display device where a box 602 is displayed to initiate an information-gathering session. After the person 102 places his or her finger on the display 402 where the box 602 is displayed, the capacitive touch sensors 404 can detect the fluctuations in capacitance that result from the person 102's heartbeat and produce raw capacitance data indicative of the fluctuations. When enough data has been collected to make a determination of the person 102's heart rate (e.g., after 10 seconds), the HR detection manager 414 can cause the user interface 600 to be updated to indicate that the person 102 can remove his or her finger from the display 402, terminating the information-gathering session. When the person 102's heart rate is determined in this way it can be used as a statistical reference or baseline by the HR detection manager 414 to determine the person 102's heart rate implicitly at later times. Furthermore, the determined heart rate can be synchronized on a server and across multiple touch devices so that the person 102's baseline heart rate is kept up to date.

The HR detection manager 414 can also cause a user interface to be displayed that indicates the person 102's determined heart rate. FIG. 7 depicts a user interface 700 that presents the determined heart rate of the person 102. The user interface 700 also presents other statistics, including the person 102's highest recorded heart rate during the information-gathering session, the person 102's lowest recorded heart rate during the information gathering session, and a date of the information-gathering session. In the illustrated example, the user interface 700 also includes a 'Playback Waveform' indication 702. The playback waveform indication 702 represents functionality that allows the person 102 to select to playback their heartbeat waveform. Playback of the person 102's heartbeat waveform can comprise an animation in which a line indicative of the aggregated capacitance is "drawn" onto the display over time.

Although the user interface 600 is not illustrated with the information included in the user interface 700, in one or more embodiments the user interface 600 can be configured to include at least some of that information. For example, the user interface 600 may be configured to include the determined heart rate, such that the person 102's heart rate is presented on the user interface 600 in substantially real time.

The person 102's substantially real-time heart rate can be presented as part of the user interface 600 graphically or in text. By "substantially real-time" it is meant that there is at least some delay (minimally perceptible) between detection of capacitance fluctuations in the person 102's hand due to his or her heartbeat by the capacitive touch sensors 404 and presentation of the determined heart rate via the user interface 600. The illustrated user interfaces 600 and 700 should not be seen to limit the user interfaces that can be displayed by an application that explicitly determines the person 102's heart rate. An application used to explicitly determine the person 102's heart rate may cause the presentation of a variety of differently configured user interfaces to prompt the user to make contact with the computing device 106 and display results indicative of the determined heart rate without departing from the spirit or scope of the techniques described herein.

In addition to the explicit determination described just above and to implicit determinations in which the person 102 interacts with the computing device 106, a determination of the person 102's heart rate can also be made while the display 402 of the computing device 106 is in a power-saving mode as in FIG. 2. In this scenario, the display 402 may not display anything—it may simply be black. The person 102 may nevertheless contact the display 402 with a portion of his or her hand, e.g., while simply holding the computing device 106. While the person 102 contacts the display 402 that is in such a power-saving mode, the capacitive touch sensors 404 of the computing device can still detect fluctuations in capacitance due to the person 102's heartbeat. Accordingly, the HR detection manager 414 can process the raw capacitance data produced responsive to detecting contact with the display while it is in a power-saving mode (e.g., sleeping, hibernating, off, etc.) to determine the heart rate of the person 102.

In another example of implicit heart rate determination, the HR detection manager 414 determines the person 102's heart rate opportunistically. To determine the person 102's heart rate "opportunistically", the HR detection manager 414 limits making heart rate determinations to times when it is confident that the capacitance fluctuations due to heart rate can be separated from other touch input to the computing device 106. When the HR detection manager 414 is not confident that it can separate the capacitance fluctuations due to heart rate from those due to other touch input (e.g., when there is typing activity at 60 taps per minute), the HR detection manager 414 can simply skip making a determination of the person 102's heart rate until a next opportunity. This occurs, for instance, when the frequency range of the other touch input (e.g., the 60 taps per minute) overlaps with the frequency range of valid heart beats (e.g., regularly 1-3 Hz, but in extreme cases 0.5-4 Hz). In one or more implementations, the HR detection manager 414 leverages knowledge of the activity being performed by the person 102 with the computing device 106 while implicitly determining the person 102's heart rate. By knowing the activity that the user is performing (e.g., typing at 60 taps per minute), the HR detection manager 414 can separate the touch inputs for the activity from the capacitance fluctuations caused by the person 102's heartbeat. In another example, the computing device 106 can be unlocked from a locked state with input of a known gesture. Since the unlock gesture is known, the HR detection manager 414 can leverage this information to separate the signals indicative of the known unlock gesture from a signal indicative of the person 102's heart rate.

Regardless of whether the person 102's heart rate is determined explicitly or implicitly, at some point after the heart rate is determined it can be displayed to the person via the display 402. In addition to informing the person 102 of his or her heart rate via display, the determined heart rate can be used in a variety of other ways. By way of example, the heart rate determined during interactions with the computing device 106 can serve as a signal of system usability, user engagement or mental workload, built into the interaction process itself, as a basis of system and interface change, and so on. Consider an example in which the person 102's heart rate is determined while playing a game on the computing device 106. The determined heart rate can be used by the computing device 106 to adjust a level of the game. Consider another example in which completion of a task on the computing device 106 can involve more or fewer interaction steps, e.g., more steps to capture a greater amount of information or more details about the task and fewer steps to capture less information or fewer details about the task. Based on the determined heart rate, the computing device 106 can enable the user to complete the task through a greater or lesser number of interaction steps.

Heart rate detection with multi-use capacitive touch sensors leverages the periodic change of relative static permittivity (dielectric constant) of fingers during each cardiac cycle to determine the person 102's heart rate. The change of the dielectric constant caused by the arrival of new blood to the fingers can be detected by the capacitive touch sensors 404 that are also used to detect touch inputs to control operation of the computing device 106. Traditional firmware of capacitive touch sensors treat such dielectric constant changes as noise and apply filtering algorithms to remove them. The regularity and range of heart rates (e.g., regularly 1-3 Hz, but in extreme cases 0.5-4 Hz), however, can be exploited by the techniques described herein to extract heartbeat signals from the raw capacitance data produced by capacitive touch sensors. Noise incurred by other sources, such as pressure, motion, AC power, wireless signals and so on, are in different frequency ranges and can be processed out of the raw capacitance data by the HR detection manager 414.

Using heart rate detection with multi-use capacitive touch sensors techniques, heart rates can also be determined for multiple users who touch a single presence-sensitive display component. For example, multiple different users can, at a same time, touch the display 402 of the computing device 106, which is configured with touch functionality through inclusion of the capacitive touch sensor(s) 404. The HR detection manager 414 can then determine the heart rates for each of the multiple different users from the raw capacitance data that is produced by the capacitive touch sensors 404.

These and other capabilities, as well as ways in which entities of FIGS. 1-7 act and interact, are set forth in greater detail below. These entities may be further divided, combined, and so on. The environment 100 of FIG. 1 and the detailed illustrations of FIGS. 2-7 illustrate some of many possible environments capable of employing the described techniques.

Example Methods

Figure 8:
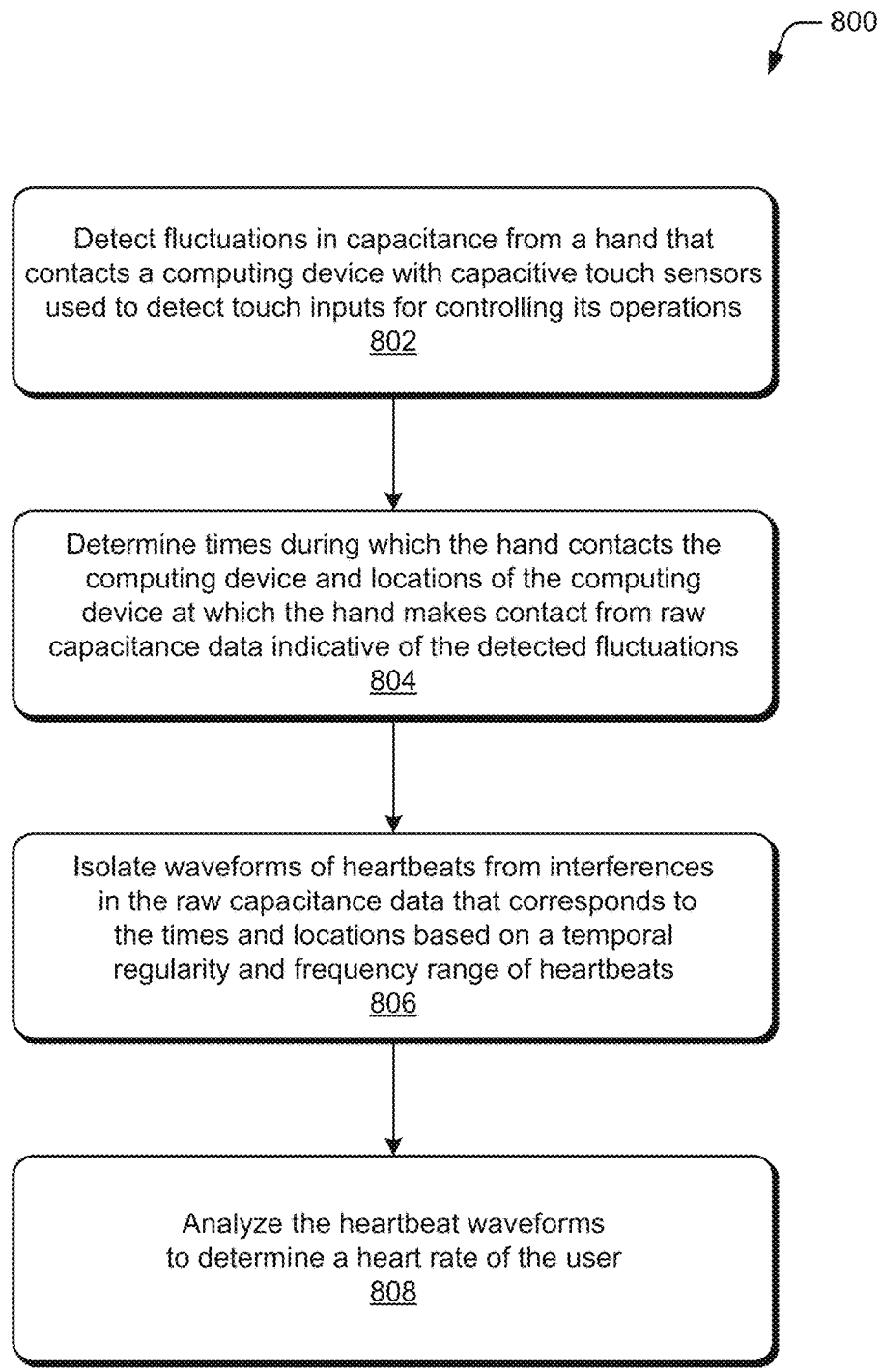
FIG. 8 illustrates a method for using multi-use capacitive touch sensors to determine a person's heart rate.
Figure 9:
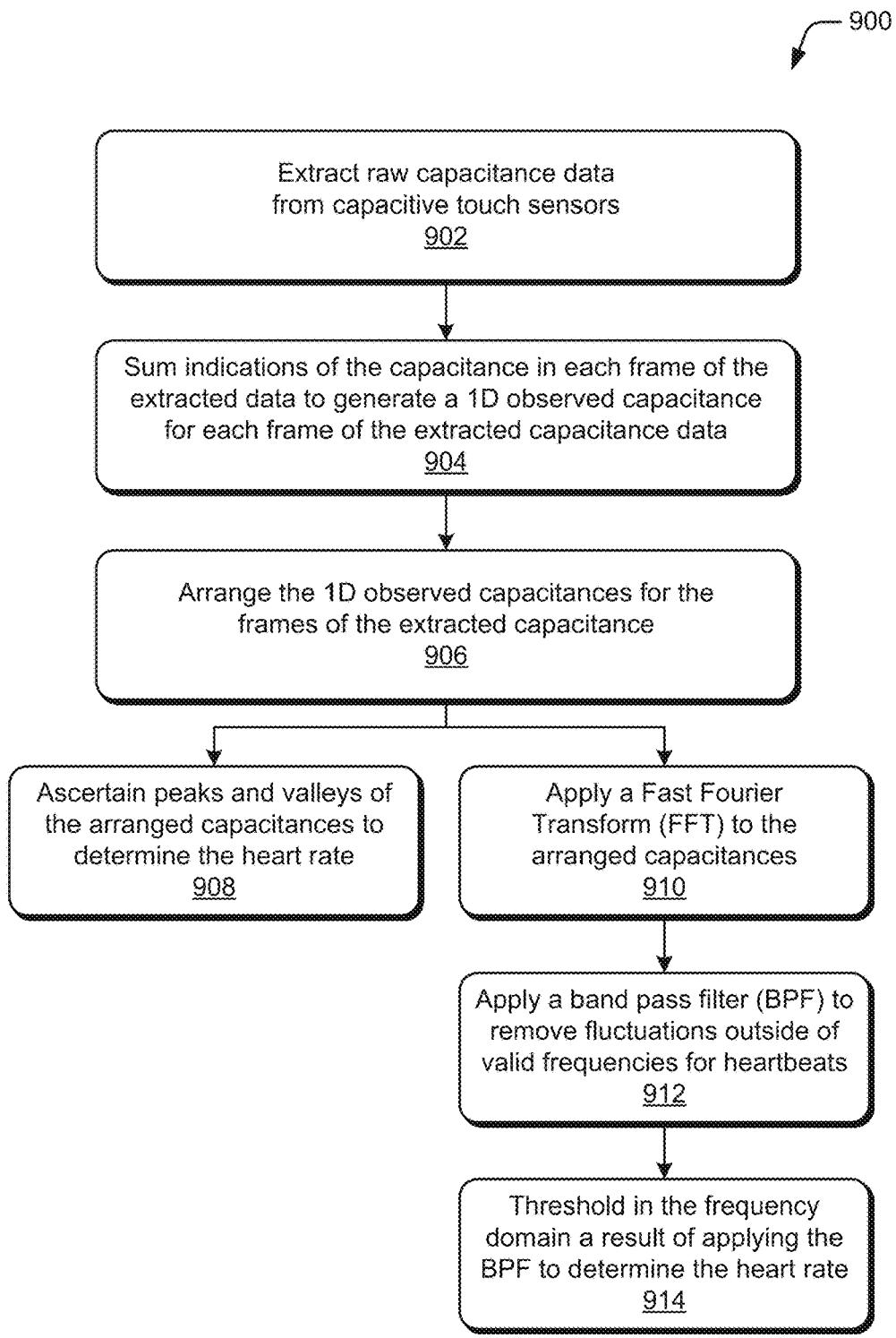
FIG. 9 illustrates a method for computing the person's heart rate from the raw capacitance data that is extracted from the capacitive touch sensors.

FIGS. 8 and 9 depict methods enabling or using heart rate detection with multi-use capacitive touch sensors. These methods are shown as sets of blocks that specify operations performed but are not necessarily limited to the order or combinations shown for performing the operations by the respective blocks. For example, the order of the blocks may be re-ordered, repeated, skipped, etc. depending on the implementation and use case. In portions of the following discussion reference may be made to environment 100 of FIG. 1 and entities detailed in FIGS. 2-7, reference to which is made for example only. The techniques are not limited to performance by one entity or multiple entities operating on one device.

FIG. 8 depicts a method 800, which describes manners in which to use multi-use capacitive touch sensors to determine a person's heart rate.

Capacitive touch sensor(s) 404 detect 802 fluctuations in capacitance from at least a portion of a user's hand in contact with a computing device 106. These capacitive touch sensors 404 are also used to detect inputs to control operations of a computing device 106. Responsive to detection of such capacitance fluctuations, the capacitive touch sensors 404 produce raw capacitance data indicative of the fluctuations detected.

Consider an example in which the person 102 interacts with the computing device 106, as is the case in FIG. 1. In this example, assume that the person 102 interacts with the computing device 106 by performing touch inputs to control operations of the computing device, e.g., the person taps keys of a keyboard displayed via the display 402 with his or her fingers to compose messages on the computing device 106. The person 102 can interact with the computing device 106 by performing other touch inputs to control its operations, such as swiping inputs, press-and-hold gestures, single-finger gestures, multi-finger gestures, hand-position gestures, and so on.

While the person 102 interacts with the computing device 106 through touch input, the capacitive touch sensors 404 detect fluctuations in capacitance, including those that occur in the person 102's hand due to his or her heartbeat. Responsive to detection of capacitance fluctuations in the person 102's hand (e.g., one or more fingers), the capacitive touch sensors 404 produce raw capacitance data that is indicative of the fluctuations detected.

A modified capacitive touch sensor driver 412 extracts the raw capacitance from the capacitive touch sensors 404. For example, the HR detection manager 414 employs the modified capacitive touch sensor driver 412 to extract the raw capacitance data from the capacitive touch sensors 404. The modified capacitive touch sensor driver 412 is modified insofar as it bypasses default configurations in touchscreen firmware and device drivers that cause fluctuations in capacitance below a certain amplitude, which includes fluctuations due to heartbeats, to be ignored. Instead, the modified capacitive touch sensor driver 412 extracts the raw capacitance data that includes indications of capacitance fluctuations due to heartbeats. The modified capacitive touch sensor driver 412 may have two modes: one that outputs raw capacitance data and another that filters out fluctuations in capacitance below a certain relative or absolute amplitude value.

An HR detection manager 414 determines 804 times during which the person's hand contacts the computing device, and locations of the computing device at which the hand makes contact. By way of example, the HR detection manager 414 determines times during which portions of the person 102's hand make contact with the computing device 106. To do so, the HR detection manager 414 uses touch events, such as POINTER_DOWN and POINTER_UP, to ascertain landing and departure timestamps of a finger of the person 102 on the display 402. The HR detection manager 414 also determines locations of the computing device 106 at which the person 102's hand makes contact. To do so, the HR detection manager 414 uses thresholding techniques to determine one or more landing points where the person 102 contacts the computing device 106. The raw capacitance data that corresponds to the locations is for a fixed size region (e.g., one inch by one inch) around the location of the computing device 106 where the person 102 is determined to make contact.

The HR detection manager 414 isolates 806 waveforms of heartbeats from interferences in the raw capacitance data that corresponds to the determined times and locations. In particular, the HR detection manager 414 isolates the heartbeat waveforms based on a temporal regularity and frequency range of heartbeats. By way of example, the HR detection manager 414 isolates the heartbeat waveform 500 that is illustrated in FIG. 5 from the extracted raw capacitance data 416. From this, the HR detection manager 414 can generate the waveform data 418 to represent the heartbeat waveform 500. The waveform data 418 can be maintained at the computing device 106 as illustrated in FIG. 4, and it can be communicated by the computing device 106 to other computing devices. By doing so, the waveform data 418 can be processed by the other computing devices. Communication of the waveform data 418 to other computing devices enables the heartbeat waveform 500 to be displayed via other computing devices, such as a computing device associated with a medical professional of the person 102.

The HR detection manager 414 analyzes 808 the heartbeat waveform to determine a heart rate of the user. By way of example, the HR detection manager 414 analyzes the heartbeat waveform 500 to determine a heart rate of the person 102. To determine the person 102's heart rate, the HR detection manager 414 can apply a variety of different techniques to the heartbeat waveform 500. The method 800 can also be applied to determine heart rates for multiple different users that make contact with the computing device at a same time.

Nonetheless, based on the determined heart rate, one or more actions are taken by the computing device or one or more services provided to the user of the computing device. By way of example, the determined heart rate serves as a signal of system usability, user engagement, or mental workload, for adjusting interaction processes, as a basis for interface change, and so on. In a particular example in which the person 102 interacts with the computing device 106 to play a game, the determined heart rate can be used to adjust a level of difficulty of the game.

In addition to being used for motion- and affect-aware interfaces, the determined heart rate of the person 102 is also used to control communication of content (e.g., advertising content) to the person 102. Consider an example in which the person 102's heart rate is determined at a first time and then at a second time that is after the first time. Assume that the person 102's heart rate determined at the first time is at a normal level (e.g., 60-100 BPM), indicating generally a normal or low level of stress. Based on this determination, advertising content can be delivered to the person 102 based on having a normal or low level of stress, such as content that advertises products or services for improving productivity, products or services that the person 102 is determined to use in association with his or her work, products or services that the person 102 is determined to use in association with homecare, and so on.

In this example, assume that the person 102's heart rate determined at the second time is at a high level (e.g., above 100 BPM) indicating an elevated level of stress. Based on this determination, advertising content can be delivered to the person 102 based on having a high level of stress, such as content that advertises vacations, products or services for relaxation, and so on. It is to be appreciated that a variety of other actions can be taken based on the determined heart rate of the person 102 without departing from the spirit or scope of the techniques described herein. By way of example, the determined heart rate can be used as a basis for alerting a medical professional associated with the person 102.

FIG. 9 depicts method 900, which describes manners in which to compute a person's heart rate from the raw capacitance data extracted from capacitive touch sensors. The method of 900 of FIG. 9 details how the raw capacitance data that is extracted from the capacitive touch sensors is processed to determine a user's heart rate. In particular, the steps of FIG. 9 that are performed after the extraction detail the isolation of the heartbeat waveforms of step 806 and the analysis to determine the heart rate of the user of step 808.

The HR detection manager 414 extracts 902 raw capacitance data from capacitive touch sensors. This raw capacitance data indicates fluctuations in capacitance caused by a user's heartbeat as well as other sources such as AC charger noise, LCD noise, florescent light bulbs, electromagnetic interference, and other artifacts. By way of example, the HR detection manager 414 employs the modified capacitive touch sensor driver 412 to extract the raw capacitance data from the capacitive touch sensors 404.

The HR detection manager 414 sums 904 indications of capacitance in each frame of the extracted data to generate a one-dimensional (1D) aggregated capacitance for each frame of the extracted capacitance data. By way of example, the HR detection manager 414 sums indications of the capacitance in each frame of the extracted raw capacitance data 416. By summing the individual indications of capacitance, the HR detection manager 414 generates a 1D aggregated capacitance for each frame of the extracted raw capacitance data 416.

The HR detection manager 414 arranges 906 the 1D aggregated capacitances for the frames of the extracted capacitance data. By way of example, the HR detection manager 414 arranges the 1D aggregated capacitances generated at step 904 using timestamps associated with the frames of the extracted raw capacitance data 416.

The heart rate is then determined from the 1D aggregated capacitances for the frames of the extracted capacitance data. The techniques described below are two ways in which the heart rate of the person 102 may be determined from the capacitances, although other techniques may be used.

In accordance with a first technique for determining a heart rate, the HR detection manager 414 performs a time domain analysis. To do so, the HR detection manager ascertains 908 peaks and valleys of the arranged capacitances to determine the heart rate. The ascertained peaks and valleys are indicative of the person 102's heart rate.

A second technique for determining a heart rate from the 1D aggregated capacitances involves performing a frequency domain analysis in which a determination of the heart rate is made in the frequency domain. The HR detection manager 414 applies 910 a Fast Fourier Transform (FFT) to the 1D arranged capacitances. By way of example, the HR detection manager 414 applies an FFT to the 1D aggregated capacitances arranged at step 906, the result of which is a Discrete Fourier Transform.

The HR detection manager 414 applies 912 a band pass filter to remove fluctuations in capacitance that are outside of a range for valid human heartbeats. For example, the HR detection manager 414 applies the band pass filter to the result of application of the FFT that is produced at 910. In one or more implementations, the band pass filter is set to pass the capacitance fluctuations that are within a range of 0.5-4 Hz to account for human heart rates between 30 and 240 BPM.

The HR detection manager 414 thresholds 914 a result of applying the band pass filter in the frequency domain to determine the heart rate. Given the result of step 912, for instance, the HR detection manager 414 thresholds the result in the frequency domain to determine the heart rate of the person 102.

The preceding discussion describes methods relating to heart rate detection with multi-use capacitive touch sensors. Aspects of these methods may be implemented in hardware (e.g., fixed logic circuitry), firmware, software, manual processing, or any combination thereof. These techniques may be embodied on one or more of the entities shown in FIGS. 1, 2, 4, and 10 (computing system 1000 is described in FIG. 10 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 10:
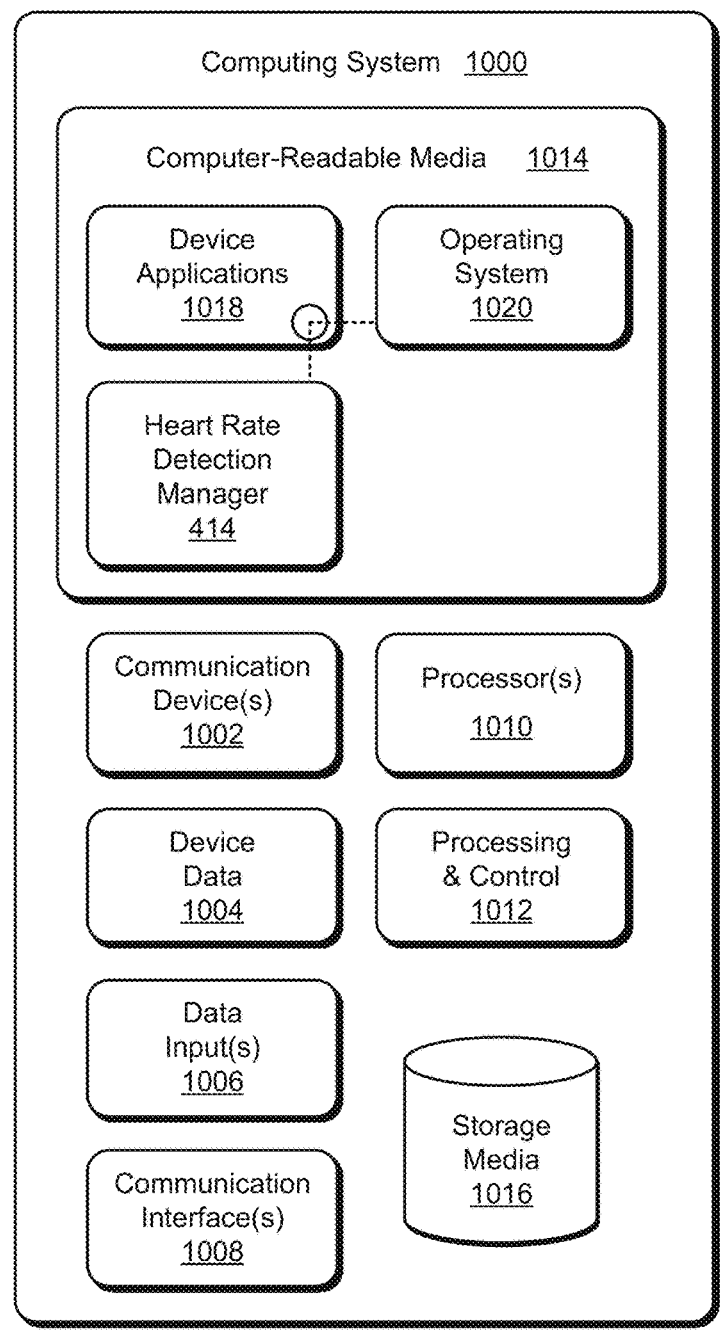
FIG. 10 illustrates an example computing system embodying, or in which techniques may be implemented that enable use of, heart rate detection with multi-use capacitive touch sensors.

FIG. 10 illustrates various components of example computing system 1000 that can be implemented as any type of client, server, and/or computing device as described with reference to the previous FIGS. 1-9 to implement heart rate detection with multi-use capacitive touch sensors. In embodiments, the computing system 1000 can be implemented as one or a combination of a wired and/or wireless wearable device, System-on-Chip (SoC), and/or as another type of device or portion thereof. The computing system 1000 may also be associated with a user (e.g., a person) and/or an entity that operates the device such that a device describes logical devices that include users, software, firmware, and/or a combination of devices.

The computing system 1000 includes communication devices 1002 that enable wired and/or wireless communication of device data 1004 (e.g., received data, data that is being received, data scheduled for broadcast, data packets of the data, etc.). The device data 1004 or other device content can include configuration settings of the device, media content stored on the device, and/or information associated with a user of the device. Media content stored on the computing system 1000 can include any type of audio, video, and/or image data, including complex or detailed results of automated nursing assessment acts. The computing system 1000 includes one or more data inputs 1006 via which any type of data, media content, and/or inputs can be received, such as human utterances, user-selectable inputs (explicit or implicit), messages, music, television media content, recorded video content, and any other type of audio, video, and/or image data received from any content and/or data source.

The computing system 1000 also includes communication interfaces 1008, which can be implemented as any one or more of a serial and/or parallel interface, a wireless interface, any type of network interface, a modem, and as any other type of communication interface. The communication interfaces 1008 provide a connection and/or communication links between the computing system 1000 and a communication network by which other electronic, computing, and communication devices communicate data with the computing system 1000.

The computing system 1000 includes one or more processors 1010 (e.g., any of microprocessors, controllers, and the like), which process various computer-executable instructions to control the operation of the computing system 1000 and to enable techniques for, or in which can be embodied, heart rate detection with multi-use capacitive touch sensors. Alternatively or in addition, the computing system 1000 can be implemented with any one or combination of hardware, firmware, or fixed logic circuitry that is implemented in connection with processing and control circuits which are generally identified at 1012. Although not shown, the computing system 1000 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

The computing system 1000 also includes computer-readable media 1014, such as one or more memory components that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage component. A disk storage component may be implemented as any type of magnetic or optical storage component, such as a hard disk drive, a recordable and/or rewriteable compact disc (CD), any type of a digital versatile disc (DVD), and the like. The computing system 1000 can also include a mass storage media component 1016.

The computer-readable media 1014 provides data storage mechanisms to store the device data 1004, as well as various device applications 1018 and any other types of information and/or data related to operational aspects of the computing system 1000. For example, an operating system 1020 can be maintained as a computer application with the computer-readable media 1014 and executed on the processors 1010. The device applications 1018 may include a device manager, such as any form of a control application, software application, signal-processing and control module, code that is native to a particular device, a hardware abstraction layer for a particular device, and so on.

The device applications 1018 also include any system components, engines, or managers to implement the techniques. In this example, the device applications 1018 include the heart rate detection manager 414.

CONCLUSION

Although embodiments of techniques using, and apparatuses enabling, heart rate detection with multi-use capacitive touch sensors have been described in language specific to features and/or methods, it is to be understood that the subject of the appended claims is not necessarily limited to the specific features or methods described. Rather, the specific features and methods are disclosed as example implementations of these techniques.

What is claimed is:

1. A method comprising:
   detecting user contact with capacitive touch sensors of a computing device, the capacitive touch sensors configured to detect touch inputs to control operations of the computing device;
   detecting, at the capacitive touch sensors and corresponding to the user contact, fluctuations in capacitance;
   extracting, based on the detected fluctuations in capacitance, raw capacitance data;
   isolating, from the extracted raw capacitance data corresponding to the user contact, heartbeat waveform data, at least a portion of the heartbeat waveform data comprising interference raw capacitance data;
   determining, based on the isolated heartbeat waveform data, a heart rate of the user; and
   communicating content corresponding to the determination of the heart rate, including configuring the content differently for different determined heart rates.

2. The method as described in claim 1, further comprising:
   summing indications of the fluctuations in capacitance in each frame of the raw capacitance data to generate a one-dimensional aggregated capacitance for a frame of the extracted capacitance data; and
   arranging the one-dimensional aggregated capacitances for each of the frames of the raw capacitance data to isolate the heartbeat waveform data.

3. The method as described in claim 1, wherein the heartbeat waveform data is isolated according to a time domain analysis.

4. The method as described in claim 1, wherein the heartbeat waveform data is isolated according to a frequency domain analysis.

5. The method as described in claim 4, wherein the frequency domain analysis comprises making a determination of the heart rate in a frequency domain by:
   determining, from the extracted raw capacitance data, times corresponding to the user contact with the capacitive touch sensors and locations corresponding to the user contact with the capacitive touch sensors;
   applying a Fast Fourier Transform to the raw capacitance data that corresponds to the times and the locations; and
   applying a band pass filter to a result of applying the Fast Fourier Transform to remove the detected capacitance fluctuations that are outside a frequency range for human heart rates wherein determining the heart rate of the user includes thresholding, in the frequency domain, a result of applying the band pass filter.

6. The method as described in claim 5, wherein the band pass filter is set to pass the detected capacitance fluctuations within a range of 0.5 hertz to 4 hertz to account for the human heart rates between 30 beats-per-minute and 240 beats-per-minute.

7. The method as described in claim 1, wherein the detected fluctuations in capacitance are detected from a finger of the user that contacts a touch-enabled display device of the computing device, the touch-enabled display device including the capacitive touch sensors.

8. The method as described in claim 1, wherein the touch inputs to control the operations of the computing device include at least one of:
   tap inputs;
   swiping inputs;
   press-and-hold gestures;
   single-finger gestures;
   multi-finger gestures; or
   hand-position gestures.

9. The method as described in claim 1, further comprising determining heart rates of multiple different users that make contact with the computing device at a same time.

10. The method as described in claim 1, further comprising determining, from the extracted raw capacitance data, locations corresponding to the user contact with the capacitive touch sensors and wherein the raw capacitance data that corresponds to the locations indicates the capacitance fluctuations that are detected within a fixed-size region around the locations of the user contact with the capacitive touch sensors of the computing device.

11. The method as described in claim 1, further comprising displaying a user interface at a predetermined time that prompts the user to make contact with a touch-enabled display device of the computing device, the touch-enabled display device including the capacitive touch sensors.

12. The method as described in claim 1, wherein the interference raw capacitance data comprises a portion of the raw capacitance data separate from another portion of the raw capacitance data corresponding to the touch inputs to control operations of the computing device.

13. The method as described in claim 1, further comprising:
detecting second user contact with capacitive touch sensors of the computing device;
detecting, at the capacitive touch sensors and corresponding to the second user contact, second fluctuations in capacitance;
extracting, based on the detected second fluctuations in capacitance, second raw capacitance data;
isolating, from the extracted second raw capacitance data corresponding to the second user contact, second heartbeat waveform data, at least a portion of the second heartbeat waveform data comprising second interference raw capacitance data;
determining, based on the isolated second heartbeat waveform data, a second heart rate of the user; and
communicating second content corresponding to the determination of the second heart rate, including configuring the second content differently than the content.

14. A device comprising:
one or more capacitive touch sensors configured to detect touch inputs to control operations of the device and used to:
detect, from user contact with the capacitive touch sensors of the device, fluctuations in capacitance; and
produce raw capacitance data indicative of the detected fluctuations;
a modified device driver, coupled to the one or more capacitive touch sensors, to extract the raw capacitance data;
a processing system, coupled to the modified device driver, to implement a heart rate detection manager configured to:
process the extracted raw capacitance data;
isolate, from the extracted raw capacitance data, heartbeat waveform data, at least a portion of the heartbeat waveform data comprising interference raw capacitance data;
determine a heart rate of the user from the isolated heartbeat waveform data; and
communicate content corresponding to the determination of the heart rate, including configuring the content differently for different determined heart rates; and
a presence-sensitive display component configured to display the communication of content corresponding to the determined heart rate of the user.

15. The device as described in claim 14, wherein the extracted raw capacitance data is processed according to a time domain analysis or a frequency domain analysis to determine the heart rate of the user.

16. The device as described in claim 14 wherein:
the presence-sensitive display component comprises the one or more capacitive touch sensors;
the one or more capacitive touch sensors detect the fluctuations in capacitance from contact made by the user with the presence-sensitive display component; and
the heart rate detection manager is further configured to present a user interface via the presence-sensitive display component that prompts the user to make contact with the presence-sensitive display component using a portion of the user's hand.

17. The device as described in claim 14, wherein the heart rate is determined in a background while the operations of the device are performed according to the touch inputs.

18. A computer-implemented method comprising:
determining, from raw capacitance data in association with a first time, a first heart rate of a user, the raw capacitance data corresponding to fluctuations in capacitance received at one or more capacitive touch sensors of a computing device that are used to detect touch inputs to control operations of the computing device, at least a portion of the raw capacitance data comprising interference raw capacitance data;
receiving first content for output by the computing device, the first content based on the first heart rate determined in association with the first time;
determining, from the raw capacitance data produced by the one or more capacitive touch sensors in association with a second time, a second heart rate of the user;
receiving second content for output by the computing device, the second content based on the second heart rate determined in association with the second time; and
communicating first content corresponding to the determination of the first heart rate and second content corresponding to the determination of the second heart rate.

19. The method as described in claim 18, wherein the first heart rate or the second heart rate is determined in a background while the operations of the computing device are performed according to the touch inputs.

20. The method as described in claim 18, wherein the first heart rate or the second heart rate is determined from the raw capacitance data produced responsive to detection of contact made by a hand of the user with a display device of the computing device that is in a power-saving mode.

* * * * *